United States Patent
Buysch et al.

[11] Patent Number: 5,670,029
[45] Date of Patent: Sep. 23, 1997

[54] PROCESS FOR THE SEPARATION OF A MIXTURE OF BENZYL CHLORIDE, BENZYL ALCOHOL, DIBENZYL ETHER AND AQUEOUS HYDROCHLORIC ACID

[75] Inventors: Hans-Josef Buysch; Ursula Jansen; Pieter Ooms, all of Krefeld; Erhard-Günther Hoffmann, Ratigen; Bernd-Ulrich Schenke, Bottrop, all of Germany

[73] Assignee: Bayer Aktiengesellschaft, Leverkusen, Germany

[21] Appl. No.: 724,651

[22] Filed: Oct. 3, 1996

[30] Foreign Application Priority Data

Oct. 10, 1995 [DE] Germany .................... 195 37 752.4

[51] Int. Cl.⁶ .................................................. B01D 3/10
[52] U.S. Cl. .................. 203/91; 203/99; 203/DIG. 19
[58] Field of Search .............. 203/91, 99, DIG. 19; 568/659, 699, 715

[56] References Cited

U.S. PATENT DOCUMENTS 3,715,408  2/1973  Brown et al. .................. 203/99
5,258,554  11/1993  Langer et al. .................. 568/745

FOREIGN PATENT DOCUMENTS 872525  10/1981  U.S.S.R. .

*Primary Examiner*—Virginia Manoharan
*Attorney, Agent, or Firm*—Sprung Horn Kramer & Woods

[57] ABSTRACT

A process for the separation of a mixture which contains benzyl chloride, benzyl alcohol, dibenzyl ether and aqueous hydrochloric acid, wherein said mixture is continuously introduced via a side-feed into a distillation column from which aqueous hydrochloric acid and benzyl chloride are continuously taken off as overhead product, benzyl alcohol and dibenzyl ether are continuously taken off as bottom product, thereby the formation of dibenzyl ether is reduced or virtually prevented.

12 Claims, 1 Drawing Sheet

PROCESS FOR THE SEPARATION OF A MIXTURE OF BENZYL CHLORIDE, BENZYL ALCOHOL, DIBENZYL ETHER AND AQUEOUS HYDROCHLORIC ACID

The present invention relates to a process for the continuous separation by distillation of mixtures of benzyl chloride, benzyl alcohol, dibenzyl ether and aqueous hydrochloric acid, as are typically formed in the hydrolysis of benzyl chloride with water to give benzyl alcohol.

BACKGROUND OF THE INVENTION

Processes described in the literature for the preparation of benzyl alcohol by hydrolysis of benzyl chloride generally employ homogeneous mixtures of benzyl chloride, water and a water-soluble solubilizer, such as alcohol, acetone, dioxane or acetic acid (J. Chem. Soc. 1954, 1840; Ibid. 1957, 4747); the possibility of substantial hydrolysis of the benzyl chloride in such processes is set against the necessity of a complex separation by distillation. The hydrolysis of benzyl chloride in the presence of alkalis or alkali (alkaline earth) metal carbonates has also been described (J. Am. Chem. Soc. 62 (1940), 2481). The presence of such alkaline hydrolysing media accelerates the hydrolysis. At the same time, the reaction can be brought to complete conversion. However, a disadvantage in the alkaline saponification is the production of large amounts of aqueous waste liquors containing unreacted alkaline hydrolysing media and sodium chloride formed. Disposal of such waste liquors is laborious and expensive.

In the salt-free hydrolysis of benzyl chloride with water, without bases, according to a still unpublished process, an incomplete conversion of about 35–99% is carried out and then the aqueous phase is separated from the organic phase. The latter depending on the conversion rate, comprises variable proportions of benzyl chloride, benzyl alcohol, dibenzyl ether and residues of aqueous hydrochloric acid, which are soluble in the organic phase or which have not been completely separated off.

In the said processes, in addition to the desired benzyl alcohol, dibenzyl ether also always occurs as reaction product; its formation apparently proceeds in the basic region by condensation of previously formed benzyl alcohol and still unhydrolysed benzyl chloride. However, this condensation takes place not only during the hydrolysis reaction, but also proceeds during the work-up by distillation of a hydrolysis mixture of this type, as soon as the content of benzyl chloride is above 1% (Chem. Prum. 32 (1982), 586; cited in C.A. 98:106 890). In order to suppress this secondary formation of dibenzyl ether occurring during the distillation, a complex reaction of residues of benzyl chloride with nitrogen compounds is recommended, for example with hexamethylenetetramine (CS 216 042 B; cited in C.A. 102, 45606t).

SUMMARY OF THE INVENTION

It has now been found that the formation of dibenzyl ether during the distillation can be virtually avoided, if the organic phase is continuously introduced via a side-feed into a distillation column from which aqueous hydrochloric acid and benzyl chloride are continuously taken off as overhead product and benzyl alcohol and dibenzyl ether are continuously taken off as bottom product.

The invention relates to a process for the separation of a mixture which contains benzyl chloride, benzyl alcohol, dibenzyl ether and aqueous hydrochloric acid, which is characterized in that a mixture of this type is fed via a side-feed to a continuously operated distillation column having a stripping section and enrichment section, the distillation column is operated at a pressure of 1–950 mbar at the top of the column, and at the top of the distillation column a mixture which essentially comprises benzyl chloride and aqueous hydrochloric acid is taken off and from the bottom of the distillation column a mixture which essentially comprises benzyl alcohol and dibenzyl ether is taken off.

According to the invention, mixtures containing the said constituents which originate from the most varied sources can be used. However, mixtures to be used usually originate from the hydrolysis of benzyl chloride for the preparation of benzyl alcohol. In particular, these are hydrolysis mixtures which have been subjected to a preliminary separation into an aqueous and an organic phase, the organic phase being used according to the invention. Mixtures to be used generally comprise 1–65% by weight of benzyl chloride, 34–98% by weight of benzyl alcohol, 0.5–12% by weight of dibenzyl ether and 0.5–12% by weight of aqueous hydrochloric acid, preferably 9–60% by weight of benzyl chloride, 39–90% by weight of benzyl alcohol, 0.5–10% by weight of dibenzyl ether and 0.5–10% by weight of aqueous hydrochloric acid, particularly preferably 24–55% by weight of benzyl chloride, 44–75% by weight of benzyl alcohol, 0.5–8% by weight of dibenzyl ether and 0.5–8% by weight of aqueous hydrochloric acid. All percentages are based in this case on the total weight of the said four constituents.

Depending on the conversion rate of the benzyl chloride to be hydrolysed and on the amount of water used, the aqueous hydrochloric acid present in the mixture to be used contains 0.01–23% by weight of hydrogen chloride.

The mixture to be used and to be separated according to the invention is fed via a side-feed to a continuously operated distillation Column. The distillation column is operated at a pressure of 1–950 mbar, preferably 10–500 mbar, particularly preferably 20–300 , mbar at the top of the column. In this case, in a manner known to those skilled in the art, as a function of the top pressure set and as a function of the composition of the mixture to be separated, a temperature in the bottom of 30°–200° C., preferably 60°–180° C., particularly preferably 70°–165° C., is established. In a corresponding manner, an overhead temperature of 20°–175° C., preferably 50°–155° C., particularly preferably 60°–140° C., is established. The overhead temperature in this case is always below the bottom temperature. The side feeding to be performed according to the invention of the mixture to be separated is performed at a point of the distillation column at which a temperature of 25°–195° C., preferably 55°–175° C., particularly preferably 65°–160° C., prevails. The establishment of a temperature gradient is known to those skilled in the art. It is dependent, inter alia, on the composition of the mixture and on its preheating. In the context of the process according to the invention, the distillation column can be operated with a loading of 0.05–1.0 kg of organic phase in the mixture to be separated per liter of void volume of the column per hour. Preferably a loading of 0.15–0.9 kg/l·h, particularly preferably 0.25–0.8 kg/l·h, is set.

The additional formation of dibenzyl ether is virtually prevented according to the invention and decreased to low values of less than 4%, preferably less than 2%, particularly preferably less than 0.5%, based on the amount of benzyl alcohol.

BRIEF DESCRIPTION OF THE DRAWINGS

FIG. 1 shows as mass streams: the starting mixture to be separated (1), the overhead product (2), comprising aqueous hydrochloric acid (2a) and benzyl chloride (2b), a reflux line (3) to the column (I), and the bottom product (4), comprising benzyl alcohol and dibenzyl ether. (I) can be a distillation column having known internals such as bubble-cap trays, sieve ways etc., or a distillation column packed with packings. Columns of this type are likewise known to those skilled in the art.

Figure 1:
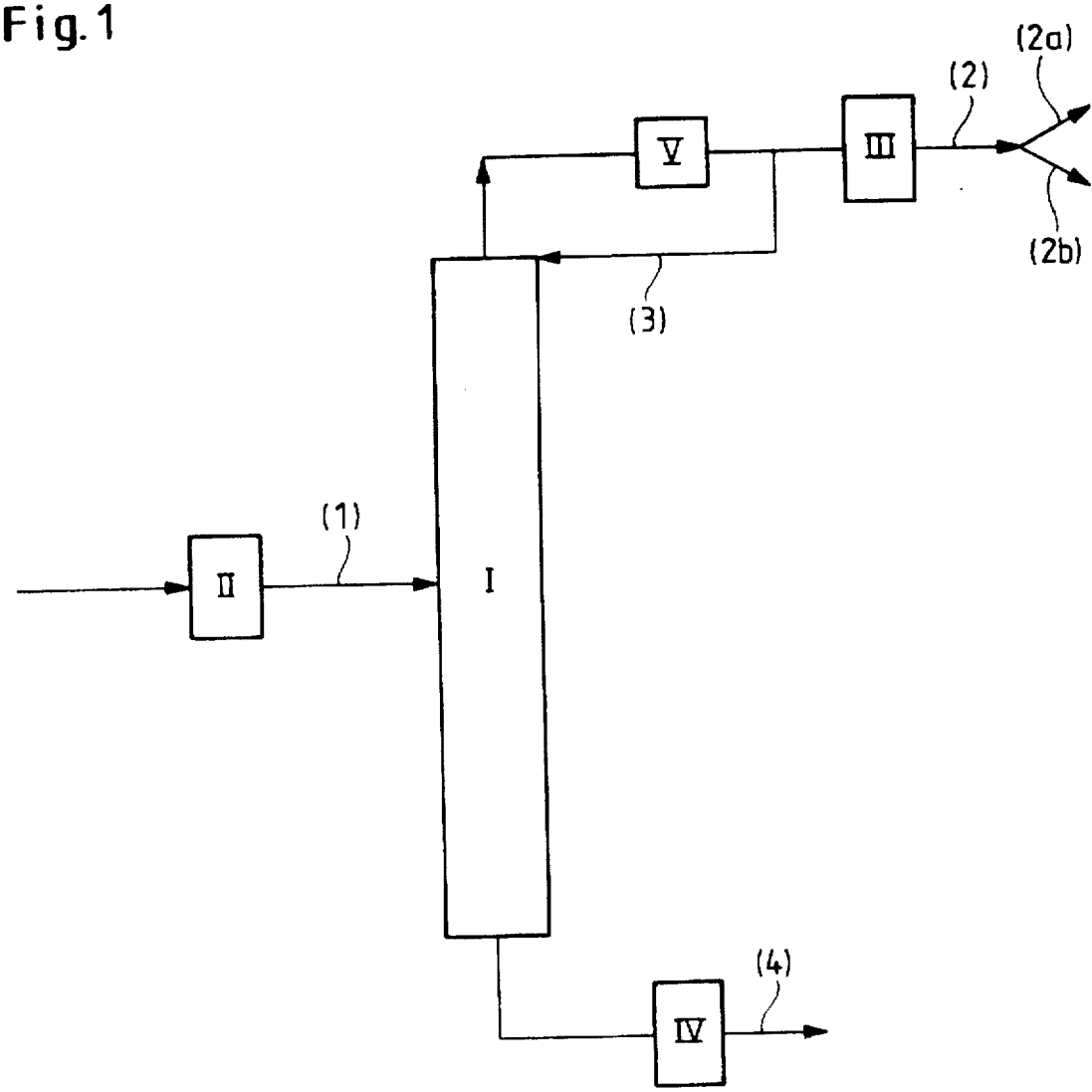
FIG. 1 shows a pictorial schematic for carrying out the process of the invention. It contains, as apparatus: a distillation column (I), a feed pump for the mixtures to be separated (II), two pumps (III+IV) for removing the overhead product and bottom product respectively, a condense for the overhead product (V).

The bottom product can be separated into the desired benzyl alcohol and the by-product dibenzyl ether in a manner known to those skilled in the art, for example by distillation, crystallization or freezing out. The overhead product can be separated into benzyl chloride and aqueous hydrochloric acid in a manner likewise known to those skilled in the art, for example by decanting. The benzyl chloride can be recycled to the hydrolysis. The aqueous hydrochloric acid can likewise be supplied for utilization known to those skilled in the art.

In comparison with the prior art, the process of the invention offers a number of advantages:

a) residues of benzyl chloride in the hydrolysis mixture do not have to be laboriously removed by chemical reactions;
b) it is possible by means of the continuous side-feed and vacuum distillation of a hydrolysis mixture to suppress virtually completely the additional formation of dibenzyl ether in the manner specified above;
c) simultaneously, a virtually complete separation of the benzyl chloride from the benzyl alcohol is achieved, so that the content of benzyl chloride is below 50 ppm.

EXAMPLES

Example 1

The reaction apparatus which was used was a distillation column having side feed, which comprised a stripping section and an enrichment section. To start up the column, the bottom was charged with pure benzyl alcohol and heated to 142° C. at 100 mbar. As soon as a temperature of 135° C. had been reached at the feed-in point, addition of a mixture of 35% by weight of benzyl chloride, 57% by weight of benzyl alcohol, 4% by weight of dibenzyl ether and 4% by weight of 3% strength hydrochloric acid was started. The loading was 0.145 kg/l-h. Benzyl chloride and dilute hydrochloric acid distilled off overhead at a temperature of 104° C., while benzyl alcohol and dibenzyl ether passed into the bottom product, from where they were continuously removed. After the separation of the condensed overhead product into aqueous hydrochloric acid and organic phase, the composition of the organic phase, after the distillation equilibrium had been established, was more than 95% by weight of benzyl chloride and less than 5% by weight of benzyl alcohol. The bottom phase, in addition to benzyl alcohol, only contained dibenzyl ether in an amount of approximately 8.0% by weight, which corresponded to an increase of dibenzyl ether of 1.4% by weight, based on benzyl alcohol. Benzyl chloride could not be detected.

Example 2

A distillation as in Example 1 was carried out, but with a loading of 0.37 kg/l-h. The content of benzyl alcohol in the organic phase of the overhead fraction was less than 4% by weight, that of benzyl chloride was over 96% by weight. The benzyl chloride content of the bottom phase was less than 0.01% by weight. The increase in dibenzyl ether was 0.6% by weight, based on benzyl alcohol.

Example 3

Example 2 was repeated with a loading of 0.76 kg/l-h. The overhead fraction, after equilibrium had been established, comprised in its organic phase more than 96% by weight of benzyl chloride and less than 4% by weight of benzyl alcohol; in addition, dilute hydrochloric acid was obtained by allowing the mixture to settle. After distillation, a fraction containing more than 99% by weight of benzyl alcohol and less than 0.05% by weight of benzyl chloride was obtained from the bottom phase. The increase in dibenzyl ether was about 0.5% by weight, based on benzyl alcohol.

Example 4

Example 1 was repeated at a pressure of 50 mbar and a loading of 0.15 kg/l-h. The composition of the organic phase of the overhead product was on average 90% by weight of benzyl chloride and 10% by weight of benzyl alcohol. The bottom fraction contained less than 0.01% by weight of benzyl chloride. The increase in dibenzyl ether was about 1.2% by weight, based on benzyl alcohol.

Example 5

Example 1 was repeated at a pressure of 12 mbar and a loading of 0.11 kg/l-h. The average composition of the organic phase of the overhead product after equilibrium had been established was 85% by weight of benzyl chloride and 15% by weight of benzyl alcohol. The bottom fraction contained 0.01% by weight of benzyl chloride and less than 4.5% by weight of the total amount of dibenzyl ether.

We claim:

1. Process for the separation of a mixture which contains benzyl chloride, benzyl alcohol, dibenzyl ether and aqueous hydrochloric acid, which comprises feeding said mixture via a side-feed to a continuously operating distillation column having a stripping section and enrichment section, operated at a pressure of 1–950 mbar at the top of the column, withdrawing a mixture of benzyl chloride and aqueous hydrochloric acid from the top of the distillation column and withdrawing a mixture of benzyl alcohol and dibenzyl ether from the bottom of the column.

2. Process according to claim 1, wherein the pressure at the top of the column is 10–500 mbar.

3. Process of claim 2, wherein said pressure is 20–300 mbar.

4. Process according to claim 1, wherein the temperature of the column at the feed-in point is 25°–195° C.

5. Process of claim 4, wherein said temperature is 55°–175° C.

6. Process of claim 5, wherein said temperature is 65°–160° C.

7. Process according to claim 1, wherein a column loading of 0.05–1.0 kg per hour of organic phase per liter of void volume of the column is fed.

8. Process of claim 7, wherein said column loading is 0.15–0.9 kg/l-h.

9. Process of claim 8, wherein said column loading is 0.25–0.8 kg/l-h.

10. Process according to claim 1, wherein the mixture to be separated comprises 1–65% by weight of benzyl chloride, 34–98% by weight of benzyl alcohol, 0.5–12% by weight of dibenzyl ether and 0.5–12% by weight of aqueous hydrochloric acid based on the total weight of the four constituents.

11. Process of claim 10, wherein said mixture comprises 9–60% by weight of benzyl chloride, 39–90% by weight of benzyl alcohol, 0.5–10% by weight of dibenzyl ether and 0.5–10% by weight of aqueous hydrochloric acid.

12. Process of claim 11, wherein said mixture comprises 24–55% by weight of benzyl chloride, 44–75% by weight of benzyl alcohol, 0.5–8% by weight of dibenzyl ether and 0.5–8% by weight of aqueous hydrochloric acid.

* * * * *